United States Patent [19]

Briody

[11] 4,052,443
[45] Oct. 4, 1977

[54] PROCESS FOR PREPARING AQUEOUS SLURRIES OF TABULAR HABIT DIPERISOPHTHALIC ACID

[75] Inventor: Robert G. Briody, Corpus Christi, Tex.

[73] Assignee: PPG Industries, Inc., Pittsburgh, Pa.

[21] Appl. No.: 633,184

[22] Filed: Nov. 19, 1975

[51] Int. Cl.$^2$ .......................................... C07C 179/10
[52] U.S. Cl. ............................................... 260/502 R
[58] Field of Search .................................. 260/502 R

[56] References Cited

U.S. PATENT DOCUMENTS

| 3,639,285 | 2/1972 | Nielsen | 260/502 R |
| 3,655,738 | 4/1972 | Nielsen | 260/502 R |
| 3,880,914 | 4/1975 | Nielsen | 260/502 R |

Primary Examiner—James O. Thomas, Jr.
Assistant Examiner—W. B. Lone

[57] ABSTRACT

Aqueous slurries of acicular habit diperisophthalic acid are converted to slurries of tabular habit by heating at temperatures above 67° C.

1 Claim, 1 Drawing Figure

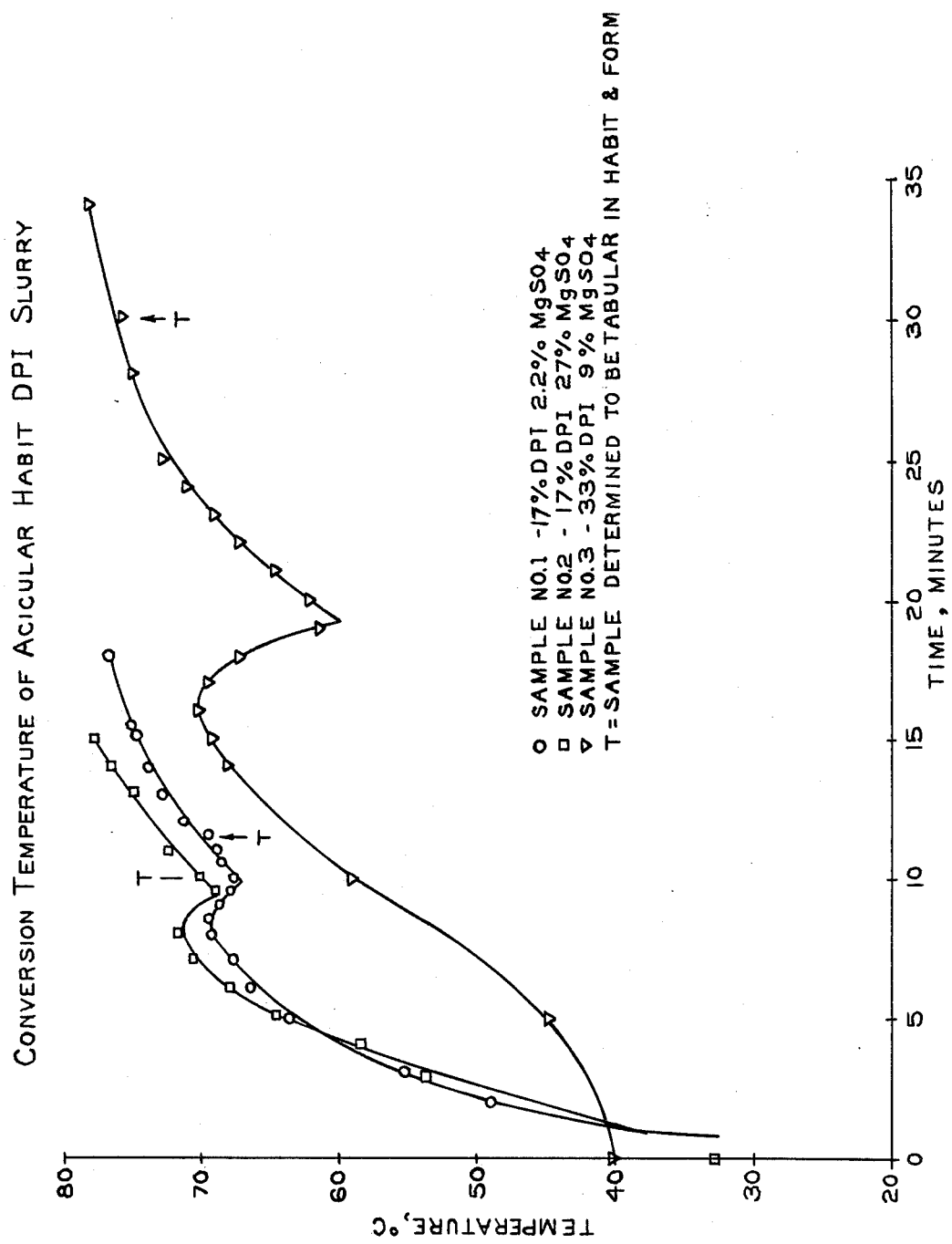

PROCESS FOR PREPARING AQUEOUS SLURRIES OF TABULAR HABIT DIPERISOPHTHALIC ACID

BACKGROUND OF THE INVENTION

Aqueous slurries of diperisophthalic acid (DPI) are useful in forming core particles for encapsulated bleaching compositions such as described in U.S. Pat No. 3,494,787 (issued to J. P. Lund and D. R. Nielsen).

DPI has been described as having two different crystal forms defined by characteristic X-ray diffraction powder pattern spacings in U.S. Pat No. 3,880,914 issued to D. R. Nielsen, which disclosure is incorporated herein by reference. Each crystal form of DPI has a symmetry of structure which is usually associated with an external symmetry or "habit." Two habits of DPI have been identified and designated as "tabular" and "acicular." The tabular habit DPI is characterized by a shape having two approximately equal dimensions with the third dimension about one-fifth to one-third the other dimensions. Tabular habit DPI has characteristic X-ray diffraction powder pattern interplanar spacings as follows:

A
9.17
5.50
4.21
3.75
3.54
3.26
3.20
3.15
2.44
2.39
2.30
1.97
1.93
1.87
1.84
1.80
1.61 with major line intensities at interplanar spacings of 4.21, 3.20 and 2.39 A. This habit is in contrast to the acicular (needlelike) habit DPI crystal having a typical length to diameter ratio of over 20 and characteristic X-ray diffraction powder pattern interplanar spacings as follows:

A
8.47
5.59
5.33
4.64
4.54
4.23
3.71
3.63
3.46
3.40
3.32
3.24
3.19
3.06
2.82
2.78
2.73
2.68
2.60
2.48
2.40
2.27
2.21
2.16
2.15 with major line intensities at interplanar spacings of 5.59, 4.23 and 3.66 A.

Practical differences reside in the use of aqueous DPI slurries having acicular or tabular crystal habit. The acicular habit crystal as a consequence of its geometry has a tendency to compact or "set-up" in a water slurry with the result that it promotes stoppages in pumps, transfer lines, and related equipment. In contrast to the acicular crystal, an aqueous slurry of tabular habit DPI is pumped and hydraulically transported with relative ease.

U.S. Pat. No. 3,655,738 (issued to D. R. Nielsen) describes (Example 3) a process of reacting isophthalic acid and hydrogen peroxide in methanesulfonic acid, cooling the reaction medium to 40° C., centrifuging to separate solid DPI product and water washing the product to give tabular form DPI product having the associated tabular habit external crystal shape. It is desirable to prepare tabular habit DPI/water mixtures without the necessity of using a specific synthesis method. In particular, the metastable nature of aqueous slurries of tabular habit DPI make it desirable to devise a method of easily converting acicular habit DPI/water mixtures into tabular habit DPI/water mixtures.

THE INVENTION

This invention relates to the preparation of tabular habit DPI. More particularly, it pertains to a convenient and effective means for preparing an aqueous slurry of tabular habit DPI from an aqueous slurry of acicular habit crystal by subjecting an aqueous slurry of acicular habit DPI to a temperature of at least about 67° C. Thus, by virtue of this invention an acicular habit DPI/aqueous slurry is transformed with relative ease and without serious loss of DPI into a more utile tabular habit DPI/aqueous slurry.

DETAILED DESCRIPTION OF THE INVENTION

Aqueous Slurries of DPI

Formation of the aqueous tabular habit DPI slurry pursuant to this invention is achieved with slurries of almost any concentration of acicular habit DPI. However, as a minimum, it is generally advisable to employ a slurry with a water content over 30 weight percent (on a water plus DPI basis) to discourage hazardous decomposition. At the opposite extreme, very dilute slurries (over 90 weight percent water and less than 10 weight percent DPI) are generally uneconomical to pump and heat. Accordingly, a slurry water content between about 20 to 60 weight percent DPI (on a water plus DPI basis) is typically employed.

While normally the aqueous slurry of acicular habit DPI will contain mainly acicular habit DPI, slurries containing both acicular as well as tabular habit DPI can be employed. Since below 67° C., the tabular habit tends to be metastable and revert to acicular habit, especially if acicular habit DPI is also present, the availability of slurries containing significant proportions of both habits is small.

Conversion to the tabular habit according to this invention is not adversely effected by the presence in the slurry of other materials such as dispersing agents (see application Ser. No. 360,858, filed May 16, 1973 now abandoned), for example, magnesium sulfate, sodium sulfate, sodium chloride; or stabilizing agents to prevent a high pH environment (see U.S. Pat. No. 3,770,816 issued to D. R. Nielsen).

Heating of the slurry to effect conversion is performed by warming the acicular habit DPI/water mixture which is initially at a temperature below 67° C., typically by any conventional means such as electric heating cables, hot water jackets, etc. It is preferred practice to heat the slurry no faster than will allow for approximately uniform temperatures (and to avoid localized overheating) to be attained throughout the mass of the slurry. The slurry is maintained at the temperature above about 67° C. until transformation to tabular habit is accomplished, and usually until the DPI content of the slurry is substantially exclusively in the tabular form and habit. Since in the presence of even small amounts of acicular habit DPI, the tabular habit has a tendency to convert to acicular habit essentially complete conversion to tabular habit is desirable.

Transition of acicular habit DPI/water slurry to a tabular habit slurry occurs at a minimum temperature of about 67° C. and is usually completed at temperatures under 80° C. The slurry may be heated to higher temperatures up to about 90° C., but it is preferable to avoid heating the DPI slurry for longer periods and at higher temperatures than necessary to effect crystal transformation from acicular to tabular habit since the DPI decomposition rate increases rapidly with increasing temperature.

Determination of precisely when conversion from acicular habit to tabular habit slurry occurs above the temperature of about 67° C. is possible by a variety of methods. The slurry may be continuously sampled while heating above the minimum conversion temperature and the DPI content observed with the aid of a microscope to ascertain if the crystal habit has changed. As a preferred method, batches of aqueous acicular slurry may be heated at a relatively uniform rate and the rate of temperature rise of the slurry recorded. It has been found that when the crystal habit converts from acicular to tabular the rate of temperature rise abruptly decreases and displays an endothermic response. When the rate of temperature rise resumes a steady rate of increase, experience indicates the slurry has undergone conversion to the tabular habit. In addition, conversion to tabular habit is accompanied by a noticeable reduction in viscosity of the slurry and this effect serves as an approximate indication of transition from acicular to tabular habit DPI.

Below the temperature of about 67° C., the aqueous tabular DPI slurry is metastable and may revert to acicular form. This reversion is encouraged if acicular seed crystals are contacted with the ambient temperature tabular slurry. Should reversion take place the slurry may be returned to tabular habit by heating past the critical conversion temperature until evidence of crystal transformation is obtained.

The following examples illustrate the manner in which this invention may be practiced.

EXAMPLE I 1000 ml. of aqueous slurry of acicular habit DPI containing varying proportions of magnesium sulfate were placed in a 2000 ml. beaker and heated at a uniform rate with continuous stirring while observing the temperature of the slurry. Each slurry was analyzed for crystal form by X-ray powder pattern analysis and for crystal habit by microscopic examination both before and after the heat treatment was performed.

The results are graphically displayed in the FIG. 1. As shown therein, when an aqueous slurry of acicular crystal is gradually heated and measurements of temperature vs. time are taken at appropriate intervals a clear endotherm indicative of DPI crystal transformation from acicular to tabular is observed. It was noted that the slurries were increasingly viscous during heating until the stage of conversion to tabular habit at which point the slurries exhibited a greatly reduced viscosity and were stirred with relative ease.

EXAMPLE II

Experiment A

Approximately 15 grams of aqueous slurry having a total solids content of 48.8 weight percent of 94.2 weight percent acicular DPI was heated in a screw-capped 15 ml. vial for 5 hours in a temperature range of 65.4° to 66.3° C.

Experiment B

Approximately 15 grams of aqueous slurry having a total solids content of 48.8 weight percent of 94.2 weight percent DPI was heated in a screw-capped 15 ml. vial for 2 hours in a temperature range of 76.8° to 77.5° C.

The DIP content of the slurries prior to heating in Experiments A and B was all of the acicular form and habit as shown by X-ray diffraction and microscopic observation. After heating for the specified period at the indicated temperature range, the X-ray diffraction and microscopic observation showed the DPI content of the sample of Experiment A still to be acicular whereas the DPI content of the sample of Experiment B was substantially all of tabular habit and form.

This demonstrates that temperature for conversion of slurries of acicular DPI to tabular DPI is above 66° C.

Although the present invention has been described with reference to the specific details of particular embodiments thereof, it is not intended to limit the scope of the invention except insofar as the specific details are recited in the appended claim.

I claim:

1. A method of preparing an aqueous slurry of metastable tabular habit diperisophthalic acid said slurry consisting essentially of diperisophthalic acid and water which comprises maintaining an aqueous slurry containing acicular habit diperisophthalic acid and having a water content of over 30 weight percent at a temperature from above 67° C. to about 90° C. whereby to convert acicular diperisophthalic acid to tabular habit diperisophthalic acid.

* * * * *